United States Patent [19]

Reubke

[11] 4,054,587
[45] Oct. 18, 1977

[54] PREPARATION OF CHLOROANTHRAQUINONES FROM NITROANTHRAQUINONES

[75] Inventor: Karl-Julius Reubke, Cologne, Germany

[73] Assignee: Bayer Aktiengesellschaft, Leverkusen, Germany

[21] Appl. No.: 680,406

[22] Filed: Apr. 26, 1976

[30] Foreign Application Priority Data

May 17, 1975 Germany .............................. 2522177

[51] Int. Cl.$^2$ .......................... C09B 1/00; C09B 1/10
[52] U.S. Cl. .................................. 260/384; 260/378; 260/379; 260/380; 260/381; 260/383
[58] Field of Search ......................................... 260/384

[56] References Cited

PUBLICATIONS

Lubs, "The Chemistry of Synthetic Dyes and Pigments", Hafner Publishing Co., N.Y. (1955), p. 345.

*Primary Examiner*—Paul F. Shaver
*Attorney, Agent, or Firm*—Burgess, Dinklage & Sprung

[57] ABSTRACT

The nitro group of an α-nitroanthraquinone is replaced by chlorine by reaction with an ionic chloride in a solvent in the presence of an acid or of a compound which eliminates an acid. The ionic chloride may be an alkali metal, alkaline earth metal, ammonium or quaternary ammonium chloride. A molten tertiary amine hydrochloride can function as the ionic chloride, the acid and the solvent. The process permits one or more nitro groups of a poly-α-nitroanthraquinone to be selectively replaced.

10 Claims, No Drawings

PREPARATION OF CHLOROANTHRAQUINONES FROM NITROANTHRAQUINONES

The subject of the invention is a new process for replacing nitro groups in anthraquinone derivatives by chlorine, using ionic chloride in the presence of acids.

It is known that nitro groups in anthraquinone can be replaced by chlorine, using elementary chlorine in suitable solvents, for example trichlorobenzene (German Patent Specification No. 252,578), or in salt melts (U.S.S.R. Patent Specification 178,390), using thionyl chloride without a solvent (German Patent Specification 280,739) or using organic compounds which eliminate chlorine, for example carbon tetrachloride under pressure (A.A. Ponomarenko, Dopovidi Akad. Nauk. Ukr. R.S.R. 1963, 787; CA 59, 12665 h).

If two nitro groups are present, such as in dinitroanthraquinones, both nitro groups are replaced. α-Chloro-α'-nitroanthraquinones have hitherto not been producible frm α,α'-dinitro-anthraquinones; these interesting compounds have hitherto been obtained, for example, by nitration of anthraquinone-1-sulfonic acid and subsequent replacement of the sulfo group by chlorine according to known processes (for example U.S. Patent Specification 2,421,837).

It is also known that a nitro group in 1,5-dihydroxy-4,8-dinitro-anthraquinone can be replaced using elementary chlorine in a mixture of boric acid/sulfuric acid in the presence of aliphatic alcohols (Japanese Patent Specification No. 72/37,252).

The procedure using elementary chlorine, agents which eliminate chlorine and the customary chlorinating agents, such as thionyl chloride, have disadvantages because, in addition to replacement of nitro groups, a substitution of hydrogen by chlorine with the formation of undesirably byproducts generally additionally takes place. Furthermore, these chlorinating agents are corrosive and difficult to handle.

If the nitroanthraquinone contains further substituents, for example amino, acylamino and/or alkoxy groups, the nitro group can then be replaced by chlorine only by the roundabout route via reduction, diazotization and a Sandmeyer reaction. This procedure is complicated and leads to product losses.

When two nitro groups are present it is not possible to replace only one nitro group by chlorine except by the special process according to Japanese Pat. Specification No. 72/37,252.

The object of the present invention is therefore to provide a generally applicable process for the preparation of α-chloroanthraquinones in which the disadvantages of the processes known hitherto are avoided.

According to the invention, a process for the preparation of an α-chloroanthraquinone is provided wherein the corresponding α-nitro compound is reacted, in a solvent, in the presence of an acid or a compound which eliminates an acid, with ionic chlorides at elevated temperature.

Compounds which are suitable for use in the process according to the invention are, for example, α-nitro compounds of the general formulae I and II.

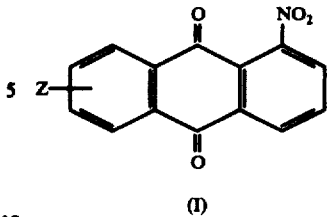

(I)

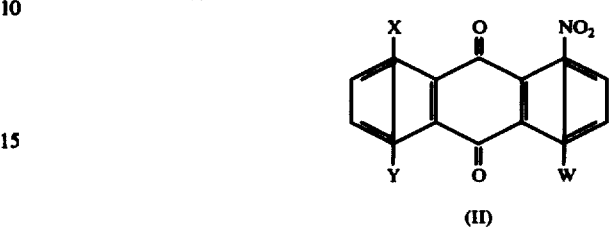

(II)

The substituent Z in formula I can be a nitro, hydroxyl, alkoxy, aryloxy, amino, alkyl, aryl, aralkyl, acylamino, sulfonic acid, sulfonamide or sulfonic ester group in the 5-, 6-, 7- or 8-position.

The substituents W, X and Y in the formula II can be hydroxyl, alkoxy, aryloxy, amino, alkyl, aryl, aralkyl or acylamino groups X and Y can also be a nitro group or a hydrogen atom, either X or Y always being a nitro group.

Suitable alkyl groups for the substituents Z, X, Y and/or W are, for example, those with 1 to 12 C atoms, especially methyl, ethyl, propyl or dodecyl groups, which optionally can contain further substituents, for example halogen, amino, monoalkylamino and/or dialkylamino groups.

Suitable aryl groups for the substituents Z, X, Y and/or W are, for example, phenyl and/or naphthyl radicals which optionally can be substituted by halogen, $C_1$ to $C_{12}$-alkyl or $C_1$–$C_4$-alkoxy groups.

Suitable acylamino groups for the substituents Z, X, Y and/or W are, for example, alkylcarbonylamino and/or arylcarbonylamino groups and alkylsulfonylamino and/or arylsulfonylamino groups, possible alkyl and aryl radicals being those mentioned above.

Preferably, α-nitro compounds of the general formula I, in which Z denotes a nitro group in any desired position or an acylamino group in the 5- or 8-position, as well as α-nitro compounds of the general formula II, in which X or Y is a nitro group and W and X or W and Y are identical, W and X or W and Y preferably being hydroxyl groups, are employed in the process according to the invention. α-Nitro compounds which are preferentially employed in the process according to the invention are 1,5-, 1,8-, 1,6- or 1,7-dinitroanthraquinone, 1,5,4,8- or 1,8,4,5-dinitro-dihydroxyanthraquinone and 1-nitro-5- or -8-benzoylamino-anthraquinone.

Solvents which can be used for the process according to the invention are those solvents which dissolve the α-nitro compounds in an adequate amount and, under the reaction conditions, do not react, or do not react to an undesirable extent, with one of the reactants. Possible solvents are, for example, aromatic hydrocarbons, which optionally can be substituted by halogen, nitro groups and/or alkyl groups, as well as liquid sulfones and sulfoxides and also the melts of hydrochlorides of tertiary amines.

Examples of suitable aromatic hydrocarbons are: toluene, o-, m- and p-xylene, isopropylbenzene, trimethylbenzene, benzene, diethylbenzene, tetramethylbenzene, di-isopropylbenzene, isododecylbenzene, tetralin, naphthalene, methylnaphthalene, diphenyl, diphenylmethane, o-, m- and p-cymene, dibenzyl, dihydronaphthalene, 2,2'-dimethyldiphenyl, 2,3-dimethyldiphenyl, 2,4'-dimethyldiphenyl, 3,3'-dimethyldiphenyl, 1,2-dimethylnaphthalene, 1,4-dimethylnaphthalene, 1,6-dimethylnaphthalene, 1,7-dimethylnaphthalene, 1,1-diphenylethane, hexamethylbenzene, isoamylbenzene, pentamethylbenzene, 1,2,3,4-tetramethylbenzene, 1,2,3,5-tetramethylbenzene, 1,2,7-trimethylnaphthalene, 1,2,5-trimethylnaphthalene, chlorobenzene, o-dichlorobenzene, trichlorobenzene, chlorotoluene and nitrobenzene.

Liquid sulfones and sulfoxides which may be mentioned are, for example, tetramethylenesulfone and dimethylsulfoxide.

Suitable tertiary amines, which are employed in the form of the molten hydrochlorides, are, for example, trialkylamines, such as, for example, trimethylamine, triethylamine, tri-n-propylamine, dimethyl-n-alkylamine with an alkyl radical with 4 to 20 C atoms, N-alkyl-cycloalkylamines, wherein the alkyl radical has from 1 to 20 C atoms and cycloalkyl ring fom 3 to 7 C atoms, N-alkyl-N-containing heterocyclics wherein the alkyl radical has from 1 to 20 atoms such as N-methylpyrrolidine, N-ethylpyrrolidine, N-methylpiperidine and N-ethylpiperidine, dimethylbenzylamine and aromatic heterocyclic compounds containing nitrogen, such as, for example, pyridine, methylpyridine, dimethylpyridine and trimethylpyridine, quinoline and methylquinoline.

Ionic chlorides which can be used for the process according to the invention are, for example, inorganic chlorides which are adequately soluble in the solvents used in the process of the invention or inorganic chlorides rendered soluble by the addition of suitable substances. Hydrochlorides of tertiary amines or quaternary ammonium chlorides can also be employed. An exaple of an inorganic chloride with adequate solubility which may be mentioned is lithium chloride, which is adequately soluble, especially in sulfones and/or sulfoxides and/or in solvent mixtures containing sulfones and/or sulfoxides. Inorganic chlorides which in themselves are slightly soluble or insoluble in the solvents to be used can be brought into solution in a manner which is in itself known by adding a sufficient amount of substances conferring solubility. Such substances which confer solubility are, for example, monocyclic or polycyclic polyethers (see C. J. Pedersen and H. K. Frensdorff, Angew. Chemie 84, 16 (1972), Angew. Chem. internat. Edit. 11, 16 (1972).

In this way virtually all inorganic chlorides, especially alkali metal chlorides and alkaline earth metal chlorides, can be employed for the process according to the invention.

Hydrochlorides of tertiary amines which can be used are the melts of hydrochlorides of tertiary amines which have already been mentioned above as solvents. Possible quaternary ammonium salts are those which can be derived from the amines listed above, which in the form of their hydrochlorides can be used as solvents, by incorporation of an alkyl radical with, for example, 1 to 20 C atoms.

In a particular embodiment of the process according to the invention, hydrochlorides of tertiary amines or quaternary ammonium chlorides which are a constituent of a basic ion exchanger are used. Ion exchangers suitable for this purpose are, for example, synthetic anion exchangers with a condensation resin skeleton, for example m-phenylenediamine-formaldehyde condensation products or polymerization resins, for example polystyrene resins containing amino groups or pyridine resins in the chloride form, which are sufficiently stable under the reaction conditions (see R. Griessback, "Austauschadsorption in Theorie und Praxis" ("Exchange adsorption in Theory and Practice"), Berlin 1957). Ion exchangers of this type are commercially available and macroporous resins are preferred.

Any desired mineral acids, such as sulfuric acid, phosphoric acid or hydrochloric acid, can be employed as acids in the process according to the invention. Lewis acids, such as aluminum halides, antimony halides or arsenic halides, or substances which eliminate acids under the reaction conditions, such as ammonium chloride or the abovementioned hydrochlorides of tertiary amines, can also be used. Hydrochloric acid is preferably used.

When hydrochlorides of tertiary amines are used in the process according to the invention, these can be employed simultaneously as the solvent, the ionic chloride and the compound which eliminates acid. With this procedure, hydrogen chloride is preferably supplied, for example in the gaseous form, and the chloride consumed is thus replaced continuously.

The reaction temperature depends on the solubility and the reactivity of the nitro compounds employed in the solvent used. It is higher the more sparingly soluble the starting material and the fewer the electron-attracting substituents which activate the leaving nitro group. The reaction temperature is generally between 60° and 240° C. Preferably the reaction temperature is between 100° and 220° C, especially between 160° and 200° C.

The reaction time can be varied within wide limits. It generally depends on the temperature and also on the solubility and the reactivity of the starting material, as well as on the concentration of chloride ions and can be, for example, 0.1 to 20 hours. Reaction times of 2 to 10 hours are preferred.

The concentration of the starting compound is variable within wide limits. Depending on the solvent, it can be, for example, 5 to 50% by weight, preferably 10 to 25% by weight, in each case relative to the weight of the solvent. The stoichiometric ratio of nitro groups to be replaced : chloride ions can generally be 1 : 1–100 or 1 : 0,1–1 for example 1 : 0,5 to 1 : 50 and preferably 1 : 1 to 1 : 10. Ratios of 1 : less than 1 are possible only if the chloride ions consumed are continuously replaced as described above.

When acylamino-substituted nitroanthraquinones are reacted, the water of reaction is advantageously removed by suitable measures, for example azeotropic distillation, in order to prevent saponification.

The products prepared according to the process of the invention can be worked up according to processes which are in themselves known, for example by filtering the product or, if appropriate after separating off the ion exchanger, at elevated temperature by distilling off the solvent.

If the α-nitro compound employed contains 2 nitro groups, it is possible to discontinue the reaction after one nitro group has been replaced by chlorine, to work up the reaction mixture and thus to obtain α-chloro-α'-nitroanthraquinones. The time at which the reaction is to be discontinued can be determined, for example, by suitable analytical measures, such as thin layer chromatography and IR spectroscopy.

The process according to the invention can be carried out, for example, by passing hydrochloric acid into a 30% strength solution of an aromatic amine, such as pyridine or α-picoline, in a solvent, such as nitrobenzene or sulfolane, with initial cooling, until the exhaust gases give an acid reaction, then introducing 30% by weight, based on the solvent, of the nitro compound, for example 1,8-dinitro-anthraquinone and heating the mixture to 180° C while bubbling a slow stream of HCl gas through the solution. The end point of the reaction can be determined by thin layer chromatography. When only one nitro group to be replaced is present, the reaction can also be continued until the waste gases give absolutely no further nitrite reaction. In the case of 1,8-dinitro-anthraquinone, the reaction is complete after about 2 to 3 hours under the indicated conditions. After the reaction mixture has cooled, the product which has precipitated is filtered off and the filtrate can be employed direct for a further reaction. Appropriately, this reaction is carried out continuously, for example in a stirred kettle cascade, and the reaction medium is recycled after centrifuging off the product.

According to another variant, an approximately 10% strength solution of the nitro compound, for example 1,5-dihydroxy-4,8-dinitro-anthraquinone, in a suitable solvent, for example nitrobenzene or trichlorobenzene, is pre-warmed to 160° C and this solution is charged from above into an exchanger column, which is heated to 160 to 170° C and is filled with anion exchanger in the chloride form, and a slow stream of HCl is passed in from below in counter-current. The feed and the dimensions can be so selected that the reaction is complete at the bottom of the column. The solution which flows out is evaporated to dryness in an evaporator and the solvent is recycled.

Accordingly, the advantages of the process according to the invention are that the reaction is carried out without molecular chlorine, that it is possible to exchange only one nitro group in dinitroanthraquinones and thus, in a simple manner, to obtain, for example, α-chloro-α-nitroanthraquinones, and that the process can be used for those anthraquinone compounds which carry yet further subsituents. Excess chlorination with replacement of hydrogen is virtually excluded.

The process according to the invention and the advantages which can be achieved therewith are particularly surprising because it is known that for benzene derivatives replacement of a nitro group by chlorine by means of hydrochloric acid (ionic chloride) is possible only in the case of tetranitrobenzenes (E. Yu. Orlova et al in "Nitro Compounds" T. Urbanski, Ed. Pergamon, 1964) and even with trinitrobenzenes is successful only with conventional chlorinating agents, such as phosphorus oxychloride, inorganic chlorides possessing no catalytic action whatsoever (G. M. Shutov et al, Zhur. Obshsch. Khim., 37 783 (1967)).

The α-chloroanthraquinones which can be prepared according to the invention are valuable intermediate products for the preparation of dyestuffs.

EXAMPLE 1

100 g of 1,8-dinitro-anthraquinone, 28 g of LiCl and 10 g of AlCl$_3$ in 500 ml of tetramethylenesulfone are stirred for 8 hours at 200° C. After cooling, the product is filtered off, washed with water and dried.

Yield: 96 g, chlorine content 11.0% (calculated 12.3%); 7% of 1,8-dichloro-anthraquinone and 3% of 1,8-dinitro-anthraquinone.

EXAMPLE 2

300 ml of pyridine are neutralized with 450 ml of 36% strength HCl and the excess water and hydrochloric acid are distilled off until the sump temperature reaches 140° C. After diluting the melt with 1 liter of nitrobenzene, 300 g of 1,8-dinitro-anthraquinone are introduced, the mixture is heated to 180° C and this temperature is maintained for 2½ hours (dichloroanthraquinone and dinitroanthraquinone are equally strongly evident in the thin layer chromatogram). The mixture is then cooled and the product is filtered off, washed with methanol and dried.

Yield: 182 g, chlorine content 12.0%; 2% of dinitroanthraquinone and 4% dichloroanthraquinone.

EXAMPLE 3

HCl is passed into a solution of 300 g of 2-methylpyridine in 1 liter of nitrobenzene, while stirring, until the mixture gives an acid reaction. 300 g of 1,8-dinitroanthraquinone are then introduced and the mixture is heated to 180° C and stirred at this temperature for 2½ hours and a very slow stream of HCl is bubbled through the solution. After cooling, the product is filtered off, washed with methanol and dried.

Yield: 234 g, chlorine content 11.9% (calculated 12.3%); 3% of dichloroanthraquinone and 4% of dinitroanthraquinone.

The nitrobenzene/picoline hydrochloride filtrate can be used again for further batches. 1-Chloro-5-nitroanthraquinone can be prepared fom 1,5-dinitro-anthraquinone in a completely analogous manner. The reaction time is 4 hours, the yield 217 g and the chlorine content 12.7%.

EXAMPLE 4

30 g of LiCl and 30 g of NH$_4$Cl are added to a suspension of 100 g of 1,8-dinitroanthraquinone in 500 g of tetramethylenesulfone at 200° C and the mixture is stirred at this temperature for a further 6 hours. After cooling, the mixture is filtered and the residue is washed with water until free from chloride. This gives 75 g of 1-chloro-8nitro-anthraquinone, Cl: : 12.0%; 5% of dichloroanthraquinone and 3% of dinitroanthraquinone.

EXAMPLE 5

HCl is passed into a solution of 30 g of 2-methylpyridine and 50 g of tetramethylenesulfone until the mixture gives an acid reaction. 30 g of 1,5-dinitro-anthraquinone are added to this melt and the mixture is stirred for 8 hours at 180° C while a slow stream of HCl is bubbled through the solution. After cooling, the product is filtered off and washed with methanol. Yield: 21 g of 1-chloro-5-nitro-anthraquinone (Cl content 12.6%, 5% of 1,5-dichloro-anthraquinone and 2% of 1,5-dinitroanthraquinone).

EXAMPLE 6

20 g of picoline in 100 ml of nitrobenzene are converted into the hydrochloride using gaseous HCl. 20 g of technical grade 1-nitroanthraquinone-8-sulfonic acid are introduced into this mixture and the mixture is heated to 180° C. After 6 hours no further nitrosulfonic acid can be detected in the chromatogram. The mixture is evaporated to dryness, the residue is dissolved in 500 ml of hot water, the solution is decolorized with 2 g of active charcoal and the sodium salt of 1-chloroanthraquinone-8-sulfonic acid is precipitated out by adding 500 ml of saturated sodium sulfate solution.

Yield: 14.2 g, chlorine content 8.7% (calculated for the Na salt of the chlorosulfonic acid: 9.85%).

EXAPLE 7

25 g of 1,5-dihydroxy-4,8-dinitro-anthraquinone, together with 25 g of a commercially available anion exchanger having quaternary ammonium chloride groups in 200 g of nitrobenzene are warmed to 180° C while a slow stream of HCl gas is bubbled through the mixture. The reaction is complete after 3 hours. The ion exchanger is filtered off. On cooling, 1,5-dihydroxy-4-chloro-8-nitro-anthraquinone precipitates out and is filtered off. Yield: 18,5 g, chlorine content 10.8% (calculated 11,1%). The ion exchanger can be directly employed for further reactions.

EXAMPLE 8

10 g of pyridine in 80 g of nitrobenzene are converted into the hydrochloride using HCl, 10 g of 1-benzoylamino-4,5-dinitro-anthraquinone are introduced into this mixture and the mixture is heated to 160° C for 4 hours. After cooling, the product is precipitated out by diluting with methanol.

Yield: 8.6 g, chlorine content 8.2% (calculated 8.7%).

It will be appreciated that the instant specification and examples are set forth by way of illustration and not limitation, and that various modifications and changes may be made without departing fom the spirit and scope of the present invention.

What is claimed is:

1. In the preparation of an α-chloroanthraquinone by reacting the corresponding α-nitro compound with a chlorinating agent in a solvent, the improvement which comprises employing an ionic chloride as said chlorinating agent and effecting the chlorination in the presence of an acid or of a compound which eliminates an acid under the reaction conditions, the ionic chloride being selected from the group consisting of inorganic chlorides soluble in the solvent under the reaction conditions, hydrochlorides of tertiary amines, quaternary ammonium chlorides and anion exchangers in the chloride form, and the acid being selected from the group consisting of a mineral acid and a Lewis acid.

2. The process according to claim 1, wherein the α-nitro compound is a dinitroanthraquinone.

3. The process according to claim 2, wherein the reaction is discontinued after one nitro group has been replaced by chlorine.

4. The process according to claim 1, wherein the ionic chloride is the hydrochloride of a tertiary amine and the reaction is effected in the presence of hydrochloric acid.

5. The process according to claim 4, wherein a melt of a hydrochloride of a tertiary amine is used simultaneously as the solvent and the ionic chloride.

6. The process according to claim 1, wherein the ionic chloride comprises an anion exchanger in the chloride form, the anionic groups comprising hydrochlorides of tertiary amines or quaternary ammonium chlorides.

7. The process according to claim 1, wherein the solvent comprises nitrobenzene or sulfolane.

8. The process according to claim 1, wherein the reaction is carried out at a temperature between about 60 and 250° C.

9. The process according to claim 8, wherein the stoichiometric ratio of nitro groups to be replaced : chloride ions is about 1 : 1–100 or 1 : 0.1–1 and the chloride ions conserved are continuously replaced.

10. The process according to claim 8 wherein the α-nitro compound has the formula

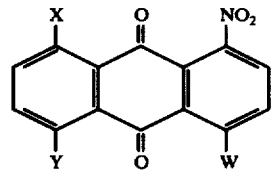

and X and W are hydroxyl.